United States Patent [19]

Markle et al.

[11] Patent Number: 5,511,547

[45] Date of Patent: Apr. 30, 1996

[54] SOLID STATE SENSORS

[75] Inventors: David R. Markle, Paoli; Misa V. Jovanovic, Wayne, both of Pa.

[73] Assignee: Biomedical Sensors, Ltd., High Wycombe, England

[21] Appl. No.: 197,423

[22] Filed: Feb. 16, 1994

[51] Int. Cl.$^6$ .................................................. A61B 5/00
[52] U.S. Cl. .................... 128/633; 422/86; 422/82.07; 436/72; 436/172
[58] Field of Search .................... 128/634, 637, 128/665, 667, 630, 633; 204/153.21; 356/39; 422/82.05, 86; 436/72, 800, 172, 68

[56] References Cited

U.S. PATENT DOCUMENTS

| | | | |
|---|---|---|---|
| Re. 32,514 | 10/1987 | Steklenski | 524/32 |
| 4,684,538 | 8/1987 | Klemarczyk | 427/54.1 |
| 4,746,751 | 5/1988 | Oviatt | 556/456 |
| 4,872,759 | 10/1989 | Stich-Baumeister | 356/432 |
| 5,030,420 | 7/1991 | Bacon | 422/82.07 |
| 5,119,463 | 6/1992 | Vurek | 385/129 |
| 5,175,016 | 12/1992 | Yafuso et al. | 427/2 |
| 5,182,353 | 1/1993 | Hui et al. | 528/31 |

*Primary Examiner*—C. Fred Rosenbaum
*Assistant Examiner*—Chalin Smith
*Attorney, Agent, or Firm*—Peter C. Richardson; Lawrence C. Akers; Mark Dryer

[57] ABSTRACT

A stabilized bio-inert sensor for the determination of an analyte, especially $pO_2$, $pCO_2$ and pH, in a medium which comprises a chemical indicator sensitive to the analyte in association with a stabilizing substrate formed from a polymer which is inert to the medium and analyte and does not affect the sensitivity of the indicator, which polymer is a cross-linked, solid silicone rubber formed from a silicone carbinol having a molecular structure compatible with said indicator.

8 Claims, No Drawings

SOLID STATE SENSORS

BACKGROUND OF THE INVENTION

This invention relates to solid state sensors. More particularly the invention is concerned with stabilized solid state sensors for the determination of concentrations of gases, especially $pO_2$ and $pCO_2$, and also, with an appropriate indicator, for the determination of pH, in liquid media, such as human blood.

The measurement in blood of $pO_2$, $pCO_2$, and pH is important during surgical procedures, post-operatively, and during hospitalization under intensive care, numerous sensor devices for the measurement and monitoring of such parameters are disclosed in the art. A sensor device, hereinafter referred to as a sensor, for determining the concentration of an analyte in a liquid medium, typically comprises an indicator having a characteristic which changes in the presence of the analyte in association with a suitable carrier or substrate which also acts as a transmission line for conveying a signal representative of said change to a suitable detector. For example, the use of pyrenebutyric acid as a fluorescent indicator for the determination of the concentration of oxygen in blood is known and the use of this sensor in conjunction with an optical fiber, wherein the fluorescent indicator is enclosed within a selectively permeable membrane, is disclosed in U.S. Pat. No. 4,476,870.

A sensor utilizing a fluorescent indicator and adapted to function satisfactorily in a biological environment should possess at least four characteristics: sensitivity, short response time, stability and bio-inertness.

Sensitivity depends upon the quantum efficiency of the fluorescent indicator, the concentration of the indicator present in the sensor and availability of the indicator to the substance, i.e. ion or gas, it must sense. Thus a sufficient amount of indicator must be available to produce a meaningful fluorescent response. However, if indicator molecules are too close together there occurs a type of behavior which is frequently detrimental to the sensor performance; this behavior is known as eximer fluorescence. Therefore, for a given indication there is an optimum indicator concentration for maximum sensitivity.

A further problem which must be solved in the construction of a fluorescent sensor is the availability of the indicator to the environment to be sensed. If the subject ions or gas cannot reach the indicator molecules the indicator will not respond to the presence or absence of said ions or gas. This problem is clearly related to the permeability of the structure in which the indicator molecules are embedded.

Also related to permeability is the response time. If the substance to be sensed (i.e. ions or gas) diffuses very slowly through the structure the response time of the sensor will be comparatively long which greatly reduces its usefulness.

A sensor for blood gas or blood pH should be capable of use over a period of many hours or days. Recalibration of a sensor which is used in vivo is clumsy and inefficient or even impossible. Thus, the stability of the sensor is a key factor in determining its utility. A common problem in existing fluorescent sensor design is the gradual loss of the indicator from the sensor. This not only reduces the sensitivity, thereby creating instability in the sensor's indication even at constant concentration of the substance being sensed but also releases a chemical indicator into the blood stream. A device which releases chemical substances into the blood stream can not be considered to be bio-inert. As used herein, the term "bio-inert" is defined to mean that characteristic of a device, i.e. a sensor, whereby any and all chemical substances which are part of the device are so securely bonded to the structure of the device that they are not released or leached away from the device under normal operating conditions.

In the prior art the problem of leaching of the indicating substance from the sensor, which is inherent when small molecules are embedded in a polymer matrix, was generally addressed by enveloping or embedding the indicator in a selectively permeable membrane.

In practice, the problem manifests itself as a progressive loss of sensitivity of the sensor as the indicator is lost; this requires a continual re-calibration of the sensor.

The stated prior art arrangement does not completely solve the problem, since a portion of the indicating substance is still leached from the sensor. Thus, the problem of re-calibration still remains, and, moreover, the released indicator goes into the patients bloodstream.

Accordingly, it is desirable to provide a sensor which is more stable in the sense that the indicator is not leached or washed away therefrom upon contact with body fluids.

The desired stability may be achieved, according to U.S. Pat. No. 5,019,350 by providing a sensor for the determination of the concentration of a dissolved substance in an aqueous medium comprising an optical fiber having a distal end to which is stably bonded an adherent, water-insoluble organic polymer having a plurality of fluorescent organic substituents, which may be the same or different, covalently bonded to said polymer through ester or amide linkages.

The combination of polymer and fluorescent organic substituents forms a fluorescent polymeric indicator, examples of which are indicators for $pO_2$, pH and $pCO_2$.

U.S. Pat. No. 5,262,037 discloses an electrochemical sensor for the determination of the partial pressure of oxygen in a bloodstream. This electrochemical sensor for $pO_2$ may be used in combination with a pH sensor and a $pCO_2$ sensor to form a multi-parameter sensor. In such a multi-parameter sensor the pH sensor and $pCO_2$ sensor preferably are made in accordance with the disclosure in U.S. Pat. No. 4,889,407 which provides an optical waveguide sensor for determining an analyte in a medium, which sensor comprises an optical waveguide having a portion to be brought into contact with the medium, said portion having a plurality of cells arranged in an array which substantially covers the cross-sectional area of the waveguide, each of said cells containing an indicator sensitive to said analyte. The preferred waveguide is an optical fiber and indicators disclosed include absorption indicators for pH, such as phenol red and fluorescent indicators, such as β-umbelliferone for pH or $pCO_2$, and pyrene butyric acid for $pO_2$. In preparing the sensor the indicator is deposited in the cells of the optical fiber in the form of a gel or solid by immersing the portion of the fiber containing the cells in a solution of the indicator and appropriate gel-forming ingredients, subjecting the immersed fibers to a vacuum so that the cells are evacuated to allow ingress of the solution and curing the gel so that the indicator is retained in the cells in a stable manner.

PCT Application Publication No. WO 91/05252 discloses a carbon dioxide monitor which comprises a substrate having thereon an indicating member comprising an intimate mixture of a transparent polymer vehicle, and an indicator material which undergoes a color change on exposure to carbon dioxide. The indicator material comprises a salt of an indicator anion and a lipophilic organic quaternary cation.

U.S. Pat. No. 5,005,572 discloses a detector for the determination of carbon dioxide in respiratory gases and a method for determining the proper placement of an intubation device in a patient's trachea. The carbon dioxide detector comprises a pH-sensitive dye, a solid phase support and a phase transport enhancer for enhancing a reaction between $H_2CO_3$ and the pH-sensitive dye.

U.S. Pat. NO. 4,728,499 discloses a combination rapid response device for the detection of carbon dioxide in a gas mixture comprising an enclosure with a transparent window having mounted therein an indicator component comprising a carder to which is fixedly attached an indicating element including a chromogenic pH-sensitive indicator which changes color when the concentration of carbon dioxide in the surrounding atmosphere exceeds 2%. The device is used to determine the correct placement of an endotracheal catheter.

It has now been found that the stability and performance of sensors for the determination of an analyte in a medium, particularly for the determination of $pO_2$, $pCO_2$ and pH in both liquid and gaseous media, is greatly enhanced when an appropriate indicator is used in association with a polymeric silicone carbinol as described hereinafter.

SUMMARY OF THE INVENTION

In accordance with the present invention there is provided a stabilized bio-inert sensor for the determination of an analyte in a medium which comprises a chemical indicator sensitive to the analyte in association with a stabilizing substrate formed from a polymer which is inert to the medium and analyte and does not affect the sensitivity of the indicator, which polymer is a cross-linked, solid silicone rubber formed from a silicone carbinol having a molecular structure compatible with said indicator.

The polymeric silicone rubber used in the sensor of the present invention is preferably one of the following two types:

1. A silicone carbinol homopolymer having the formula:

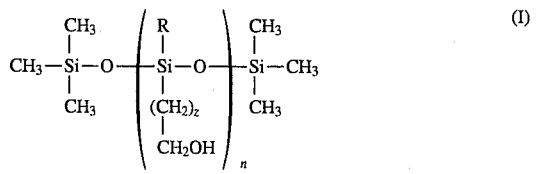

wherein R is methyl or phenyl, z in an Integer from 1 to 20 and n is an integer from 2 to 500;

2. A carbinol siloxane copolymer having the formula:

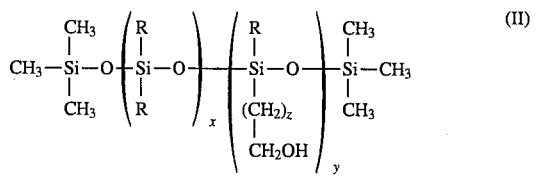

wherein each R is methyl or phenyl and the Rs may be the same or different, z is an integer from 1 to 20, and each of x and y is an integer wherein the sum of x and y is from 2 to 500.

A particularly preferred homopolymer of formula (I) is a methyl silicone carbinol homopolymer of the formula:

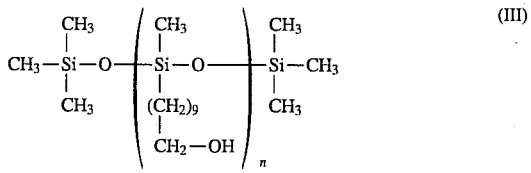

wherein n is an integer from 2 to 500.

A preferred copolymer of formula (II) is a dimethyl/methyl carbinol siloxane copolymer of the formula:

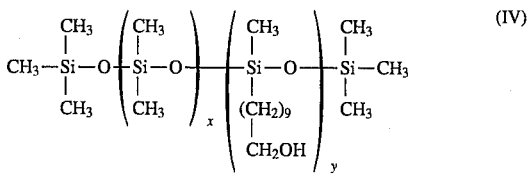

wherein each of x and y is a positive whole integer and the sum of x and y is from 2 to 500.

The above linear polymers have unique features which may be attributed to the carbinol side chains.

As used herein the term "carbinol" is a generic term to describe silicones with different alcohol side-chains. When cross-liked the carbinol groups form a hydrophobic, gas-permeable silicone matrix for the analyte-sensitive indicator associated therewith. A particularly preferred indicator is an oxygen-sensitive ruthenium indicator described hereinafter. Another preferred indicator is a carbon dioxide-sensitive indicator such as phenol red.

DETAILED DESCRIPTION OF INVENTION

The linear silicone polymer used as the substrate in the sensor according to the invention is preferably prepared by protecting a terminally unsaturated long-chain alcohol which is then used in the hydrosilation reaction (also referred to as a hydrosilylation reaction) of a selected hydrosilicone. The final step is deprotection of the alcohol-OH groups.

Reactions with similar chemistry to that of the above reaction are known in the art. For example, a hydrosilation reaction is disclosed in U.S. Pat. No. 3,122,522. However, prior to the present invention, the type of silicone polymer made in accordance with the stated reaction has not been used with analyte-sensitive indicators to make the unique sensors described herein. A particular advantageous feature of the novel sensors of the present invention is the manner whereby the silicone carbinols are cross-linked to produce solid silicone rubber-like polymers which may be tailored to be combined with different indicators to form the desired sensors.

Some of the unique and advantageous features of the materials used in the sensors of the invention are:

a) long carbinol side-chains behave as surfactants to "solubilize" the polar materials which are not soluble in water. In essence, they replace plastisizers in plasticized solid matrices which are the key elements for the $PO_2$ and $pCO_2$ sensors that are currently on the market. These solubilizing side-chains are particularly compatible with polar transition metal complexes which contain the non-polar hydrocarbon and unsaturated hydrocarbon ligands.

b) The size and length of the carbinol side-chains may be varied to change the morphology of the cross-linked solid polymer. The same polymer also may be made less hydrophobic by shortening the carbon chain length and very hydrophilic (even water-soluble) when z in Formula (I) or (II) is less than 4. The hydrophylicity of the polymer also may be controlled by combining the long chain and short chain alcohol group in the same linear prepolymer.

c) The stability of the silicone polymers and prepolymers is greatly enhanced by the polysiloxane back bone. The polymers have a high resistance to a variety of chemical agents and remain intact on long term exposures to water vapor and biological gases. The stability under gamma irradiation is comparable, if not better than, that of PVA. Some conversion of free alcohol groups to ether linkages may occur due to the formation of —O• and H• radicals.

d) The linear silicone prepolymers as well as the final polymers have no adverse affects and show no leaching of indicator elements as demonstrated by preliminary cytotoxicity studies.

Preferred embodiments of the invention are particularly describe hereinafter.

1. Polyurethane type cure system:

A "production friendly" silicone rubber matrix which incorporates an oxygen-sensitive ruthenium indicator (i.e. tris (4,7-diphenyl-1, 10-phenanthroline) ruthenium (II) chloride) and an alcohol polymer side-chain as the solubilizing environment (for the indicator) is prepared as follows: The selected prepolymer (polysilicone linear polymer to which alcohol side-chains are attached through a silicone-carbon bond) is reacted with a difunctional isocyanate in the presence of a catalyst to form a silicone matrix in which some of the alcohol groups are cross-linked through the urethane type linkage as indicated in the following equation:

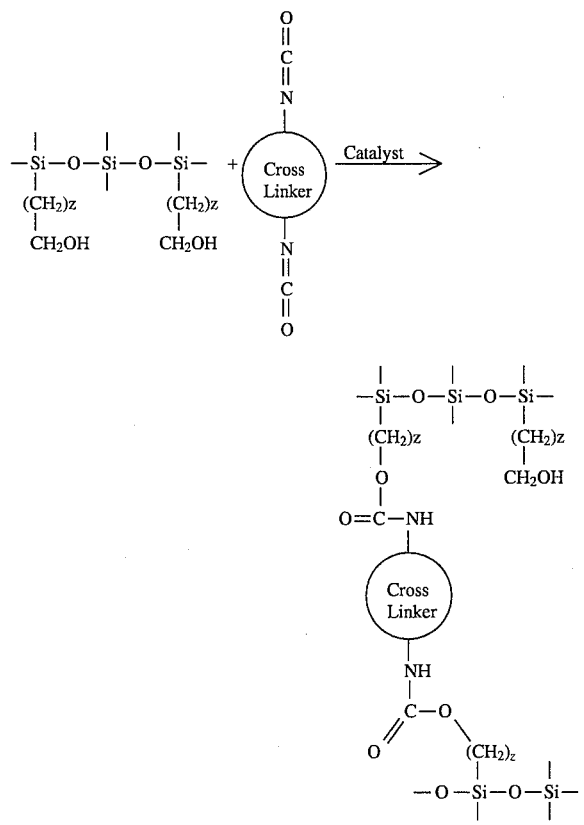

The cross-linker may be any one of a number of commercially available diisocyanates.

A preferred catalyst is dibutyltin dilaurate (DBTDL) having the formula $[CH_3(CH_2)_3]_2 Sn[O_2C(CH_2)_{10}CH_3]_2$ The low molecular weight silicone carbinol (in this and all other compounds which follow it is to be understood that carbinol is a $C_{10}$ alcohol unless specified otherwise) is combined with the ruthenium indicator which was previously dissolved in methylene chloride; the two solutions are mixed and the methylene chloride is blown off by purging the mixture with air. The use of a solvent to presolubilize the ruthenium indicator before adding it to the silicone carbinol is only for the sake of convenience and to speed up the mixing process. Alternatively, the indicator may be dissolved directly in the silicone carbinol(s) by ultrasonication.

The clear, deep red polymer precursor mixture is then combined with an appropriate difunctional isocyanate and cured in an oven at 65° C. The cure time may be shortened by substituting a more reactive aromatic isocyanate for the one currently used and/or by adding more catalyst (i.e. tolylene diisocyanate, or TDI, with a tin catalyst such as DBTDL, cures the silicone carbinol at room temperature in 2 to 10 minutes).

A typical polymer precursor mixture consists of the following:

80–90% Silicone $C_{10}$-carbinol

25mg/g of prepolymer Ruthenium indicator* presolubilized in methylene chloride and treated as described above

*polymer precursor+ cross-linker considered to be 100% of total weight; the weight of ruthenium indicator is not included and the weight of the catalyst is not considered as part of total weight unless it exceeds 1% of total weight.

10–20% dissocyante cross-linker 0.01–2% catalyst (optional—to speed up the cure)

*tris (4,7-dyphenyl-1,10-phenanthroline) ruthenium (II) chloride

Typical recipe for a thermal cure system:

900mg low molecular weight silicone $C_{10}$-carbinol homopolymer

25g Ru indicator (chloride) predissolved in methylene chloride is added and mixed with the silicone carbinol 100mg isophorone diisocyanate (IPDI), 10% by weight*

*polymer precursor+ cross-linker considered to be 100% of total weight; the weight of ruthenium indicator is not included and the weight of the catalyst is not considered as part of total weight unless it exceeds 1% of total weight.

100ml 1% of DBTDL catalyst solution in methylene dichloride (effectively 0.01% in overall catalyst concentration)

*polymer precursor+ cross-linker considered to be 100% of total weight; the weight of ruthenium indicator is not included and the weight of the catalyst is not considered as part of total weight unless it exceeds 1% of total weight.

The working life of the above mixture is 60 to 90 minutes; this may be extended by the appropriate choice of the cross-linker and the catalyst.

2. Polyether type cures:

In this embodiment it has surprisingly been discovered that certain silicone carbinols may be cured (to form solid silicone rubbers) in the presence of a tin catalyst (DBTDL), presumerably by alcohol side-chains reacting with each other and forming ether linkages.

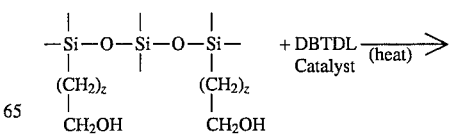

-continued

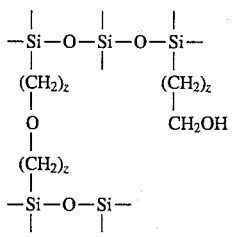

Such solids have been prepared with high molecular weight silicone carbinol homopolymers with tin catalyst concentrations of ≧ 0.5% (by wt.). Low molecular weight silicone carbinol homopolymers failed to produce a solid at low DBTDL concentrations. When making the oxygen sensor by this method, it is essential to keep the tin catalyst concentration low (not to exceed 2%) in order to prevent another side reaction from taking place. (At high concentrations of tin catalyst the solid films darken and their oxygen sensing capabilities drop, presumably because some oxidation-reduction takes place between the tin catalyst and the complexed ruthenium (II) ion).

The low molecular weight silicone carbinols may be used to prepare a solid state $pCO_2$ sensor by the above method.

3. Alcohol protecting groups (delayed cure systems):

As an extension of the above embodiments and in order to better control the curing process, it is desirable to have silicone carbinol(s) with blocked —OH groups, which, when deprotected, may undergo the same type of chemistry described above. Such protecting groups may serve as chemical and thermal switches for a chosen polymerization process.

One such example involves the use of trimethylsiloxy derivatives (TMS) which may be deprotected in situ to give the free —OH groups and initiate the polymerization.

Low and medium molecular weight TMS-protected silicone carbinols (which are also intermediates for making the corresponding carbinols) and hydrolysed TMS groups have been prepared by exposing the polymer precursor mixtures to HCl vapor.

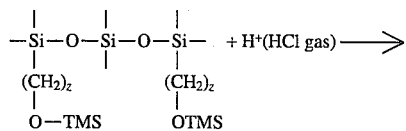

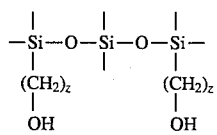

The reaction then proceeds as in methods 1 or 2 above, (or any other type of cure which involves the alcohol —OH groups).

The reaction may be conducted by placing filled fiber sensors (made from polymethyl methacrylate, PMMA, fibers) in an enclosed chamber filled with hydrogen chloride gas or by simply keeping the filled sensors above a dish containing concentrated aqueous HCl. The deprotection of the alcohol groups readily takes place at or below room temperature. In this case, it is also desirable to us fast cure conditions (TDI cross-linker with the catalyst) in order to minimize the problems which frequently accompany long cure polymerizations.

The only drawback to this approach is that once the polymerization is initiated on the surface of the polymer mixture, further polymerization is controlled by the rate of TMS group hydrolysis (i.e. diffusion rate of HCl gas through the polymer which has already formed). The poly (methyl methacrylate) fiber itself should not be affected by exposure to the HCl vapor since the conditions for its hydrolysis are quite rigorous (i.e. PMMA surface etching takes place in hot alcoholic KOH or concentrated sulfuric acid). The fiber cladding should also remain intact since it is composed of a chemically-inert perfluorinated hydrocarbon.

Other alcohol protecting groups may be used as candidates for a controlled delayed cure process.

4. UV-cure systems:

Several concepts utilized in thermal cure systems were extended to the silicone carbinols which may be UV-cured. Partial substitution of the alcohol groups with methacrylate groups provides the means for such a system; linear chain extensions and cross-linking taking place by a free-radical mechanism through the methacrylate groups.

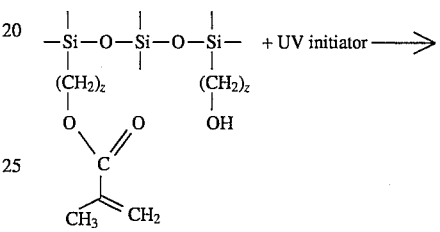

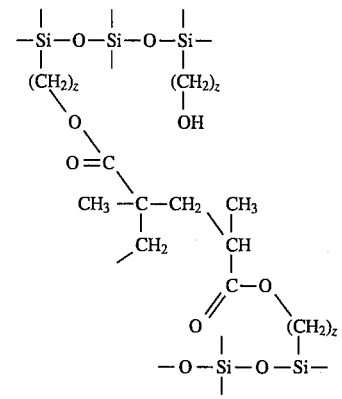

uv-initiator is benzoin isobutyl ether or any other benzoin derivative currently on the market.

Another approach is to partially esterify silicone carbinol —OH groups with methacrylic acid. Such systems have been tested with encouraging results. For instance, polydimethylsiloxane/methyl $C_{10}$-carbinol (37–40%) copolymer when completely esterified with methacrylate groups produced a hard solid when it was irradiated with UV-radiation in the presence of a liquid uv-initiator (benzoin iso-butyl ether). Several low molecular weight silicone carbinols with low methacrylate content (up to 7.5%) under the same conditions produced gels or very soft solids.

Another method involves the preparation of a low viscosity silicone $C_{10}$ carbinol homopolymer partially esterified with methacrylate groups which can be uv-cured to a gas permeable solid and still have a sufficient number of "free" carbinol side-chains left to solubilize the ruthenium indicator and provide greater flexibility and elasticity to the cured polymer. (Cross-linking through the carbon-carbon bonds usually gives more brittle solids than when the cross-linking is done through the urethane groups, or polyether linkages R-O-R. A content of about 20% of methacrylate groups on the carbinol homopolymer is generally enough to produce such a solid, leaving the remaining 80% of free carbinol chains to "soften up" the polymer).

The main disadvantages of this approach are the handling and storage of methacrylated silicones which potentially may have short shelf life (polymerization taking place prematurely if these materials are not kept at a low temperature and away from sun light). Another drawback is that this type of chemistry is not applicable to the production of solid state $pCO_2$ sensors since any radicals which are produced on exposure to the uv-radiation will destroy the pH indicator.

Some of the advantages of this process include automation of the process and setting off the cure when desired. There may also be additional advantages for making the multiple sensors on a single fiber such as combining the cure method currently used to make pH sensors with that of making the free radical initiated $pO_2$ sensor.

5. Photolabile protecting group chemistry:

As a special case of alcohol protecting groups and in conjunction with that described in 3 and 4 above, special consideration was given to using the alcohol —OH protecting groups which may be cleaved photolytically by exposure to uv-radiation. Such groups have been used successfully in sugar chemistry and to a lesser extent in genetic and DNA research.

In another embodiment ortho-nitrobenzyl ethers are chosen as prime protecting groups since, upon irradiation at $\geq$ 320 nm. for ten minutes, they give a quantitative hydrolysis of benzyl groups and a "free" alcohol. The reaction may be represented by the following equation:

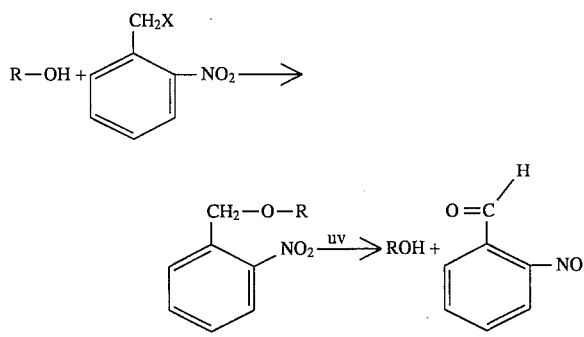

wherein ROH is an alcohol or sugar and X is chlorine or bromine.

The same type of chemistry may be extended to the silicone carbinol. Thus, a $C_{10}$-alcohol may be alkylated with 2-nitrobenzyl bromide and the resulting nitrobenzyl ether hydrolysed by exposing it to high intensity uv-radiation (as evidenced by the appearance of the —O—H stretching vibration in the ir. spectrum of the crude product).

The nitrobenzyl protected silicone carbinol is prepared directly by alkylating it with the 2-nitrobenzyl halide or by first alkylating the unsaturated alcohol and then doing the hydrosilation reaction of the nitrobenzyl-protected alcohol with hydrosilicone.

The prepolymer mixture containing the nitrobenzyl-protected silicone carbinol, ruthenium indicator, and TDI with the tin catalyst may then be irradiated with uv-radiation when the sensor fibers are filled to set off the standard, thermal cure polyurethane solid formation

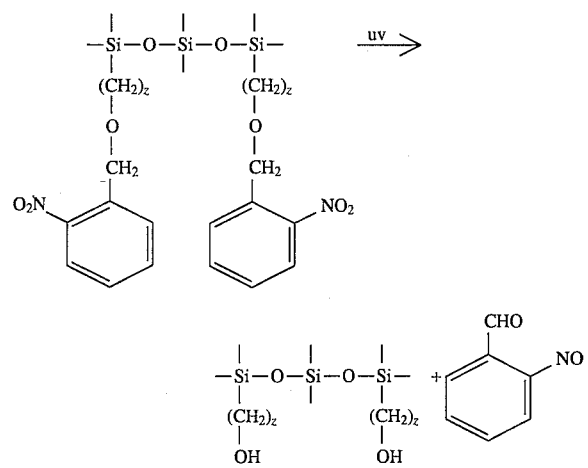

The above reaction may be followed by any of the available chemistries described above.

The by-product, ortho-nitrosobenzaldehyde stays in the matrix but it should not adversely affect the polyurethane cure. The nitrate esters may be used as alcohol protecting groups which also may be cleaved photolytically. The irradiation and subsequent decomposition thereof will produce only gaseous by-products and may be better suited for the production of the final polymer.

The following Example illustrates the preparation of an indicator-polymer combination for a $pO_2$ sensor according to the invention.

EXAMPLE

In the final polymer matrix the desired concentration of oxygen-sensitive indicator is 25 mg of indicator/gram of polymer. The polymer is made up of 80% silicone carbinol and 20% IPDI (Isophorone diisocyanate) cross linker. A stock solution of the indicator+ the silicone carbinol may be made up and kept indefinitely. The recipe for the stock solution is as follows.

1.) The weight of a 16×125 mm test tube and appropriate holding beaker was recorded.

2.) 4 grams of silicone carbinol was introduced into the test tube.

3.) In a separate beaker 0.125 grams of ruthenium (chloride form) indicator was added to 1.25 cc. of methylene chloride and completely dissolved.

4.) The indicator solution was added to the silicone carbinol and mixed well. This was done by sucking the mixture in and out of a disposable pipette.

5.) An air source was connected to the disposable tip of a 200 micro liter pipette. The tip of the pipette was placed into the test tube with the polymer/indicator mixture and air was bubbled through the mixture until all the methylene chloride was blown off as determined by weighing.

Next a 0.01% solution of DBTDL (dibutyltin dilaurate) catalyst was prepared as follows:

1.) A 1% solution was prepared by adding Add 100 micro liters of dibutyltin dilaurate (DBTDL) to 10 ml. of methylene chloride.

2.) 100 micro liters of the 1% solution was added to 10 ml. of methylene chloride to make the 0.01% solution.

The final sensor was formed by filling the cells in an optical fiber made in accordance with the procedure disclosed in U.S. Pat. No. 4,889,407 as described above. When the cells of the optical fiber sensors were ready to be filled the polymer was prepared as follows.

1.) The weight of the 10×75 mm test tube and appropriate holding breaker was recorded.

2.) 0.4 grams of stock solution (Si-carb+ indicator was introduced into test tube.

3.) 1 cc of methylene chloride was added to test tube and mixed well with a disposable pipette.

4.) 0.1 grams of IPDI was added to test tube and mixed well with same disposable pipette as above.

5.) 500 micro liters of the 0.01% DBTDL solution was added to the test tube and mixed well with the same disposable pipette as above.

6.) Methylene chloride was removed by purging the mixture with air. The mixture was weighed to determine when all the methylene chloride was removed.

It took 20 to 30 minutes to blow off all the solvent. After this time the mixture was pipetted into the cells of the $pO_2$ fibers for 60 to 90 minutes. At this time the mixture became too thick to work with. After the fibers are filled, the polymer is cured in an over at 65° C. for 24 hours. Actually, curing may take place after 2 to 3 hours but will certainly be completed in 24 hours.

The procedure described in the above Example also may be used to prepare a $pCO_2$ sensor. In a preferred embodiment a carbon dioxide-sensitive indicator is formed from an ionic complex of an organophilic quaternary ammonium cation and the anion of a sulfonephthalein dye, for example tetraoctylammonium hydroxide and Phenol Red. The indicator is incorporated into a silicone carbinol polymer matrix suitable for filling the cells of an optical fiber as described above. The polymer/indicator matrix provides a system which exhibits rapid response to changes in carbon dioxide concentration.

A multi-parameter sensor comprising an electrochemical sensor for the determination of $pO_2$, as disclosed in U.S. Pat. No. 5,262,037, in combination with a pH sensor and a $pCO_2$ sensor, made in accordance with the disclosure in U.S. Pat. No. 4,889,407 is currently manufactured by Biomedical Sensors Ltd., the assignees of the present invention. The technology of the present invention may be applied to an optical fiber structure in accordance with the disclosure in U.S. Pat. No. 4,889,407 to prepare an optical fiber $pO_2$ sensor which may replace the electrochemical $pO_2$ sensor used in the aforesaid multi-parameter sensor. Likewise the $pCO_2$ and pH sensors may be made in accordance with the present invention and the resulting multiparameter sensor, analogous in other respects to the sensor currently on the market has a number of advantages.

For example, in the preparation of $pCO_2$ sensors according to techniques disclosed in the prior art films containing the indicator are cast by allowing large amounts of solvent to evaporate. Such a casting technique does not facilitate the filling of the cells in the optical fiber because of volume loss from the solvent evaporation. Additionally, the polymers used to form the films are not very permeable to carbon dioxide and will provide a fast response only if the films are very thin and highly plasticized. Another problem with prior art technology is that the polymers and plascticizers are themselves sources of acids or bases and thus shift the pH range over which the sensor responds to $pCO_2$. For applications such as the determination of the correct placement of an endotracheal tube this latter problem is not of great significance since the film-based sensor is used primarily as a color switch. However, in a preferred embodiment of the present invention, i.e. a multi-parameter sensor incorporated in an invasive catheter for determining the concentration of analytes in a patient's blood, the color change is used as part of an analytical measurement system and any changes in the acidic and/or basic components of the polymer matrix which shift the $CO_2$-sensitive range of the matrix will compromise the accuracy of the measurements made by the sensor.

In attempts to solve the above problem a number of known silicone rubbers were examined but it was found that the indicator complex inhibited the cure of all the neutral cure silicones investigated. However, the problem was solved by using the silicone carbinol polymer of the present invention. The polymer of the present invention has no volume loss during curing, provides a neutral matrix with permeability characteristics similar to silicone and $pCO_2$ sensors made therewith provide a rapid response to changes in $CO_2$ concentration. Most significantly, the cure of the system is not affected by the presence of the indicator complex.

A number of $pCO_2$ sensors have been prepared in accordance with the present invention and the performance thereof has been very good. Depending upon the cross-linking the 90% response times vary from 75 seconds to 360 seconds with a typical modulation of 55%. This compares favorably with current sensors which have a response time of 150 to 20.0 seconds and a modulation range of 25% to 55%.

In addition to its use in a multi-parameter optical fiber sensor as described hereinabove, by incorporation of a suitable substrate, a $CO_2$ sensor prepared with a silicone carbinol polymer according to the present invention may be used in a device for the determination of the placement of an endotracheal tube in the trachea of patient, for example a device analogous to that disclosed in U.S. Pat. No. 4,728,499.

Regarding the $pO_2$ sensor described herein and illustrated in the Example, the preferred indicator tris (4,7-diphenyl-1, 10-phenanthroline) ruthenium (II) chloride was used because of its desirable physical properties and history of application in oxygen sensing technology. It has the high extinction coefficients for the two charge-transfer bands seen in the visible spectrum. The excitation wavelength is compatible with the blue LEDs currently on the market. The luminescence quantum yields are quite high ($n~0.5$) and at times may double (approach unity) when the indicator is incorporated in the polymer matrix. Besides having intense visible absorptions this indicator also has a very intense fluorescence with a remarkable Stoke's shift of $n~140$ nm. Thus, interference from reflected background light is minimal.

Both the luminescence quantum yields and luminescence efficiency are independent of the excitation wavelength. The radiative oxygen quenching constants are quite high, increasing the sensitivity towards the analyte of interest ($O_2$). Non-radiative quenching constants change in different media (solvents, polymers) but are never significant enough to overcome the radiative emissions.

The preferred indicator also is thermally, chemically and photochemically stable. Photo-bleaching over any extended period of time is minimal (particularly with the low energy light sources normally used) and this greatly increases the lifetime of the sensor. Experiments using gamma-radiation for sterilization indicated that about 20 to 25% of the indicator is decomposed, but this compares favorably with loss previously observed with other indicators.

It is to be understood that other $pO_2$ and $pCO_2$ indicators may be used in the sensors according to the invention. For example, suitable indicators for $pO_2$ determination are platinum meso-tetra(pentafluorophenyl) porphine and platinum meso-tetraphenyl porphine; and suitable $pCO_2$ indicators are cresol red and thymol blue.

We claim:

1. A stabilized, bio-inert sensor for the determination of an analyte in a medium which comprises a chemical indicator sensitive to the analyte in association with a stabilizing substrate formed from a polymer which is inert to the medium and analyte and does not affect the sensitivity of the indicator, which polymer is a crosslinked, solid silicone rubber formed from a silicone carbinol having a molecular structure compatible with said indicator.

2. A sensor according to claim 1, in which the polymer is a silicone carbinol homopolymer having the formula:

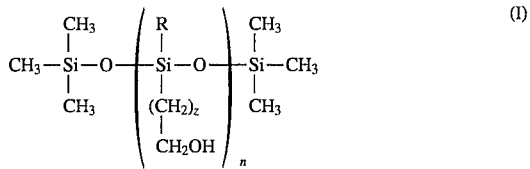
(I)

wherein R is methyl or phenyl, z in an Integer from 1 to 20 and n is an integer from 2 to 500.

3. A sensor according to claim 2, in which the polymer is a methyl silicone carbinol homopolymer of the formula:

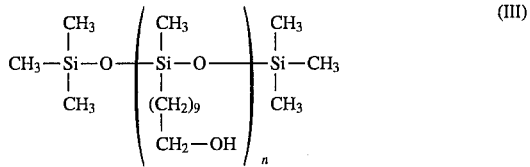
(III)

wherein n is an integer from 2 to 500.

4. A sensor according to claim 1, in which the polymer is a carbinol siloxane copolymer having the formula:

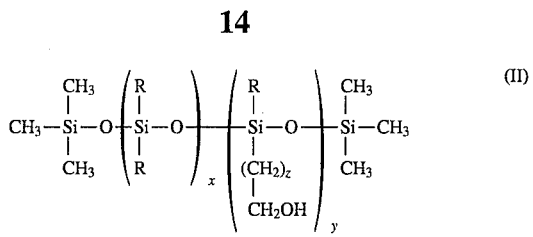
(II)

wherein each R is methyl or phenyl and the Rs may be the same or different, z is an integer from 1 to 20, and each of x and y is an integer wherein the sum of x and y is from 2 to 500.

5. A sensor according to claim 4, in which the polymer is a dimethyl/methyl carbinol siloxane copolymer of the formula:

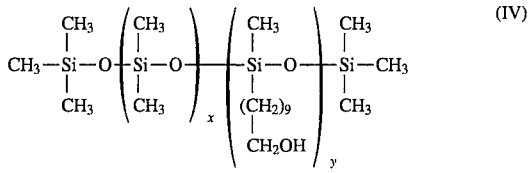
(IV)

wherein each of x and y is an integer and the sum of x and y is from 2 to 500.

6. A sensor according to claim 1 for the determination of the concentration of oxygen in a liquid medium, in which the indicator is the oxygen-sensitive fluorescent indicator tris (4,7-diphenyl-1,10-phenanthroline) ruthenium (II) chloride.

7. A sensor according to claim 1 for the determination of the concentration of carbon dioxide in a liquid or gaseous medium, in which the indicator is an ionic complex of an organophilic quaternary ammonium cation and an anion of a sulfonephthalein indicator.

8. A sensor according to claim 7, in which the organophilic quartenary ammonium cation is the cation of tetraoctylammonium hydroxide.

* * * * *